(12) United States Patent
Akashi et al.

(10) Patent No.: US 8,462,990 B2
(45) Date of Patent: Jun. 11, 2013

(54) INFRARED-RAY THERMAL IMAGE ANALYZER

(75) Inventors: Yukio Akashi, Takamatsu (JP); Kazuaki Hashimoto, Takamatsu (JP); Shogo Hayashi, Takamatsu (JP)

(73) Assignee: West Nippon Expressway Engineering Shikoku Company Limited, Takamatsu-shi (JP)

( * ) Notice: Subject to any disclaimer, the term of this patent is extended or adjusted under 35 U.S.C. 154(b) by 191 days.

(21) Appl. No.: 12/808,923

(22) PCT Filed: Oct. 21, 2008

(86) PCT No.: PCT/JP2008/069033
§ 371 (c)(1),
(2), (4) Date: Jun. 17, 2010

(87) PCT Pub. No.: WO2010/046967
PCT Pub. Date: Apr. 29, 2010

(65) Prior Publication Data
US 2010/0260374 A1    Oct. 14, 2010

(51) Int. Cl.
*G06K 9/00* (2006.01)

(52) U.S. Cl.
USPC ............................................... 382/108

(58) Field of Classification Search
USPC ................................................. 382/100, 108
See application file for complete search history.

(56) References Cited

U.S. PATENT DOCUMENTS

| | | | | |
|---|---|---|---|---|
| 5,719,395 | A * | 2/1998 | Lesniak | 250/330 |
| 5,999,843 | A * | 12/1999 | Anbar | 600/474 |
| 7,179,553 | B2 * | 2/2007 | Murphy et al. | 429/431 |
| 7,214,195 | B2 * | 5/2007 | Mitra | 600/549 |
| 7,277,744 | B2 * | 10/2007 | Schaefer et al. | 600/474 |
| 2010/0127171 | A1 * | 5/2010 | Jonsson et al. | 250/330 |

FOREIGN PATENT DOCUMENTS

| | | |
|---|---|---|
| JP | 6-201625 | 7/1994 |
| JP | 11-258188 | 9/1999 |
| JP | 2003-207472 | 7/2003 |
| JP | 2005-140622 A1 | 6/2005 |
| JP | 2005-172664 A1 | 6/2005 |
| JP | 2006-329760 A1 | 12/2006 |
| JP | 2007-163390 | 6/2007 |

OTHER PUBLICATIONS

Machine translation of Foreign document (Pub. No. JP 2005140622 A) :JP2005140622.pdf.*
International Search Report for International Application No. PCT/JP2008/069033 dated Dec. 16, 2008.
Office Action dated Feb. 23, 2012 issued in corresponding Korean Patent Application No. 10-2010-7011332 with English translation.
Refusing Reason Notice dated Mar. 13, 2012 with English translation corresponding to Japanese Patent Application No. 2009-553858.

* cited by examiner

*Primary Examiner* — Vu Le
*Assistant Examiner* — Totam Le
(74) *Attorney, Agent, or Firm* — Kratz, Quintos & Hanson, LLP

(57) ABSTRACT

The IR camera (10) takes an IR thermal image of a surface of the structure (40). In the IR thermal image, temperature gradient is superposed besides temperature difference between non-defective and defective regions of the structure. The image processing unit (21) of the analysis unit (20) produces an image indicating distribution of a temperature variation other than a temperature gradient by extracting the distribution of the temperature variation from the IR thermal image. The image display unit (30) displays the image produced by the image processing unit (21). Since the distribution of the temperature variation other than the temperature gradient is extracted from the IR thermal image, a temperature difference between defective and non-defective regions in the structure (40) can be clearly displayed. Therefore, even if there exists a temperature gradient on the structure surface, the defect location in the structure can be easily determined.

7 Claims, 13 Drawing Sheets

INFRARED-RAY THERMAL IMAGE ANALYZER

TECHNICAL FIELD

The present invention relates to an infrared-ray (IR) thermal image analyzer which enables discrimination between defective and non-defective regions included in a structure with the use of an IR thermal image of the structure taken by an IR camera. Particularly, the analyzer according to the invention enables discrimination between defective and non-defective regions even if there exists a temperature gradient on the surface of the structure.

BACKGROUND ART

Concrete structures such as bridges and viaducts (hereafter, simply referred to as "structures") not only deteriorate by themselves but also are affected by a weather variation, change in the ground, and load bearing over a course of a long period of time. These effects are accumulated, and at the time when an adverse condition occurs in addition to the accumulated effects, partial breakage or exfoliation will occur in the structure, possibly even causing an accident or damage to a third party. In order to prevent the structure from flaking, the structure must be constantly inspected and monitored.

One of methods of inspecting and monitoring a structure now under research is an infrared-ray inspection method which is capable of performing a wide range investigation highly efficiently without accessing to the structure. The infrared-ray inspection method is a method in which surface temperatures of a structure are measured with an IR camera and discrimination is made between damaged regions and non-defective regions having no damages based on the temperature differences. An IR thermal image analyzer is used in the infrared-ray inspection method.

FIG. 18 shows a basic configuration of an IR thermal image analyzer.

An IR camera 91 detects infrared ray energy emitted from an object to be measured 94 such as a structure, and takes an IR thermal image indicating temperature distribution on the surface of the object to be measured 94 by converting the detected infrared ray energy into a temperature. A display device 93 displays the IR thermal image taken by the IR camera 91.

If the object to be measured 94 has, in the inside thereof, a damaged region such as a cavity, crack or sand streak, the surface temperature of the damaged region becomes higher than the surface temperature of a non-defective region when the ambient temperature rises in daytime, for example. Therefore, if a local high-temperature region is found in the IR thermal image of the object to be measured 94 taken by the IR camera 91, it can be estimated that a damage is present in that region.

DISCLOSURE OF THE INVENTION

Problems To Be Solved by the Invention

The surface temperature of a structure is rarely uniform all over the surface, but the surface temperature of the structure often has a gradient, so-called a temperature gradient. This is attributed to the fact that the amount of heat received by the structure surface or the amount of heat emitted from the structure surface partially differs depending on the shape of the structure itself or the environment around the structure. The presence of a temperature gradient on the surface of the structure makes it difficult to discriminate between non-defective and damaged regions by the infrared ray investigation method. The reasons are described below.

FIG. 19(a) shows temperature distribution on the structure surface when there is no temperature gradient, and FIG. 19(b) shows temperature distribution on the structure surface when there is a temperature gradient. Both of FIGS. 19(a) and 19(b) show the partial temperature distribution around a defective region in the form of three-dimensional simulation images. FIG. 19(b) shows the state in which a temperature gradient of a certain magnitude is superposed on FIG. 19(a).

In FIG. 19(a), the difference is apparent between the defective region, that is, the local high-temperature region, and the non-defective region, that is, the low-temperature region. On the other hand, in FIG. 19(b), the temperature distribution in the defective region is hidden by the temperature gradient, the difference is unclear between the defective region and the non-defective region.

If an inexperienced operator takes an IR thermal image of a structure having a temperature gradient with an IR camera, it is difficult for him/her to discriminate between defective and non-defective regions based on the IR thermal image as shown in FIGS. 19(a) and 19(b).

The present invention has been made in view of the circumstances as described above, and it is an object of the invention to make it possible to easily determine the location of a defective region in a structure based on an IR thermal image even if a temperature gradient exists on the structure surface.

Means for Solving the Problems

A first aspect of the invention provides an IR thermal image analyzer including:

an IR camera for taking an IR thermal image of a structure surface;

an image processing unit for performing processing to extract, from the IR thermal image, distribution of a temperature variation other than a temperature gradient occurring on the structure surface, thereby producing an image indicating distribution of the temperature variation other than the temperature gradient; and an image display unit for displaying the image produced by the image processing unit.

The first aspect of the invention will be described with reference to FIG. 1.

In the first aspect of the invention, an IR camera 10 takes an IR thermal image of a surface of a structure 40. In the IR thermal image thus obtained, a temperature gradient is superposed on a temperature difference between non-defective and defective regions of the structure. An image processing unit 21 of an analysis unit 20 extracts distribution of a temperature variation other than a temperature gradient from the IR thermal image, thereby producing an image showing distribution of the temperature variation other than a temperature gradient. An image display unit 30 displays the image produced by the image processing unit 21.

A second aspect of the invention relates to the IR thermal image analyzer according to the first aspect, wherein the image processing unit produces an average temperature distribution image by performing moving average processing in which an average temperature is computed sequentially for each of pixel groups each consisting of a predetermined number of pixels in the IR thermal image, and produces a temperature difference image by computing a temperature difference at the same pixel between the IR thermal image and the average temperature distribution image.

The second aspect of the invention will be described with reference to FIGS. 1, 3, and 4.

In the second aspect of the invention, the image processing unit 21 divides the IR thermal image to form a group of pixels arranged in a plurality of rows and columns (see FIG. 3), and produces an average temperature distribution image by performing moving average processing to obtain an average of temperatures sequentially for each of pixel groups each consisting of a predetermined number of pixels (9×9 pixels in FIG. 3). Further, the image processing unit 21 produces a temperature difference image (FIG. 4) by computing a temperature difference at the same pixel between the IR thermal image and the average temperature distribution image. This temperature difference image is an image indicating distribution of the temperature variation other than the temperature gradient. The image display unit 30 displays this temperature difference image. When the structure includes a defective region, the image of the defective region exhibits a temperature variation which is locally increased in the temperature difference image.

A third aspect of the invention relates to the IR thermal image analyzer according to the second aspect, wherein the image processing unit performs emphasizing processing to emphasize the temperature difference in the temperature difference image, thereby producing an emphasized image in which the temperature difference in the temperature difference image is emphasized.

The third aspect will be described with reference to FIGS. 1, 7, and 9.

In the third aspect, the image processing unit 21 produces an emphasized image (FIG. 9) by performing emphasizing processing for emphasizing the temperature difference in the temperature difference image (FIG. 7), for example. This emphasized image (FIG. 9) is an image in which the temperature difference image (FIG. 7) is emphasized, and indicates distribution of a temperature variation other than a temperature gradient. The image display unit 30 displays this emphasized image. Therefore, the temperature variation amount is increased further in the image of the defective region.

A fourth aspect of the invention relates to the IR thermal image analyzer according to the second aspect, including a function storage unit for preliminarily storing an output function in which an output ratio becomes greater as an input value becomes greater, wherein the image processing unit performs emphasizing processing for emphasizing the temperature difference at each pixel in the temperature difference image by inputting the temperature difference at each pixel in the temperature difference image into the output function and thus obtaining an output value, thereby producing an emphasized image in which the temperature difference in the temperature difference image is emphasized.

The fourth aspect of the invention will be described with reference to FIGS. 1, 7, 9, and 8.

In the fourth aspect, a function storage unit 22 of an analysis unit 2 preliminarily stores an output function in which an output ratio becomes greater as an input becomes greater (FIG. 8). The image processing unit 21 performs emphasizing processing for emphasizing the temperature difference at each pixel in the temperature difference image by inputting the temperature difference at each pixel in the temperature difference image (FIG. 7) into the output function (FIG. 8) and thus obtaining an output value, and produces an emphasized image (FIG. 9). This emphasized image (FIG. 9) is an image in which the temperature difference image (FIG. 7) is emphasized, and indicates distribution of a temperature variation other than a temperature gradient. The image display unit 30 displays this emphasized image. Therefore, the temperature variation amount is increased further in the image of the defective region.

A fifth aspect of the invention relates to the IR thermal image analyzer according to the second aspect, wherein the image processing unit performs emphasizing processing for emphasizing the temperature difference in the temperature difference image by sequentially obtaining an accumulation of temperatures for each of pixel groups each consisting of a predetermined number of pixels in the temperature difference image, thereby producing an emphasized image in which the temperature difference in the temperature difference image is emphasized.

The fifth aspect of the invention will be described with reference to FIGS. 1, 7, 9, 10, and 11.

In the fifth aspect, the image processing unit 21 divides the temperature difference image (FIG. 7 or FIG. 9) to form a group of pixels arranged in a plurality of rows and columns (FIG. 10), and performs emphasizing processing for emphasizing the temperature difference in the temperature difference image (FIG. 7 or FIG. 9) by sequentially obtaining an accumulation of temperatures for each of pixel groups each consisting of a predetermined number of pixels (3×3 pixels in FIG. 10) in the temperature difference image, thereby producing an emphasized image (FIG. 11). This emphasized image (FIG. 11) is an image in which the temperature difference image (FIG. 7 or FIG. 9) is emphasized, and indicates distribution of a temperature variation other than a temperature gradient. The image display unit 30 displays this emphasized image. Therefore, the temperature variation amount is increased further in the image of the defective region.

A sixth aspect of the invention relates to the IR thermal image analyzer according to the second aspect, including a defect storage unit for preliminarily storing information indicating a correlation between a temperature variation amount in the temperature difference image and a depth of a defect located in the inside of the structure, wherein the image processing unit obtains a defect depth in a part of the produced temperature difference image where a local temperature variation occurs by using the information, and produces a defect determination image in which the display state is changed according to the obtained defect depth in the part of the temperature difference image where the local temperature variation occurs.

The sixth aspect will be described with reference to FIGS. 1, 12, 13, and 14.

The temperature difference in the temperature difference image has a correlation with the depth of a defect located in the inside of the structure.

In the sixth aspect, a defect storage unit 23 of the analysis unit 20 preliminarily stores information indicating a correlation between a temperature variation amount in the temperature difference image and a depth of a defect located in the inside of the structure.

The image processing unit 21 produces a temperature difference image (FIG. 13) based on an IR thermal image taken by the IR camera 10 (FIG. 12), and obtains a defect depth of a part of the produced temperature difference image (FIG. 13) where a local temperature variation occurs by using the information stored in the defect storage unit 23. The image processing unit 21 then produces a defect determination image (FIG. 14) in which the display state, for example the display color is changed according to the obtained defect depth in the part of the temperature difference image where a local temperature variation occurs. The image display unit 30 displays this defect determination image.

A seventh aspect of the invention relates to the IR thermal image analyzer according to the sixth aspect, wherein the image processing unit obtains a defect depth corresponding to the temperature variation amount at the center of the part of the produced temperature difference image where a local temperature variation occurs by using the correlation.

As shown in FIG. 17, the defect depth is closely related to the temperature variation amount at the center of the part in the temperature difference image where a local temperature variation occurs.

Advantageous Effects of the Invention

According to the present invention, distribution of a temperature variation other than a temperature gradient is extracted from an IR thermal image taken by an IR camera, which makes it possible to clearly display, in an image, the temperature difference between defective and non-defective regions in the structure. Therefore, even if there exists a temperature gradient on the surface of the structure, the location of a defect in the structure can be determined easily.

Further, when the structure has a defective region, the image of the defective region exhibits a local increase in temperature variation in the temperature difference image. Therefore, the defect depth can be estimated by measuring the temperature variation amount of the part where the local temperature variation occurs. If the defect depth is known, the degree of risk of flaking can be predicted.

BEST MODE FOR CARRYING OUT THE INVENTION

Exemplary embodiments of this invention will be described with reference to the accompanying drawings.

Configuration of the Embodiment

FIG. 1 is a functional block diagram showing a basic configuration of an IR thermal image analyzer according to an embodiment of the invention.

The IR thermal image analyzer 1 has an IR camera 10, an analysis unit 20, and an image display unit 30. The analysis unit 20 has an image processing unit 21, a function storage unit 22, and a defect storage unit 23. The IR camera 10 and the analysis unit 20 are communicably connected to each other through a signal line L1. The analysis unit 20 and the image display unit 30 are also communicably connected to each other through a signal line L2. The communicable connection between the IR camera 10 and the analysis unit 20 and between the analysis unit 20 and the image display unit 30 may be implemented wirelessly.

The IR camera 10 detects infrared ray energy emitted from the structure 40 and takes an IR thermal image indicating temperature distribution on the surface of the structure 40 by converting the detected infrared ray energy into a temperature.

The image processing unit 21 of the analysis unit 20 performs a series of image processing, to be described later, using the IR thermal image obtained by the IR camera 10. The function storage unit 22 stores an output function as shown in FIG. 8. The defect storage unit 23 preliminarily stores information indicating a correlation between a temperature variation amount in a temperature difference image produced by the image analysis unit 21 and a depth of a defect located in the inside of the structure.

The image display unit 30 displays an image (temperature difference image) produced by the analysis unit 20. The image display unit 30 may be a monitor or the like displaying the image on a display device, or may be a printer or the like printing the image.

Processing According To the Embodiment

FIG. 2 shows a flow of a series of processing performed by the analysis unit.

The IR camera 10 takes an IR thermal image of the surface of the structure 40. The analysis unit 20 receives an image signal relating to the IR thermal image from the IR camera 10 (Step S1). The image processing unit 21 produces an average temperature distribution image using the IR thermal image (Step S2). Further, the image processing unit 21 produces a temperature difference image by computing a temperature difference at the same pixel between the IR thermal image and the average temperature distribution image (Step S3). Further, the image processing unit 21 performs emphasizing processing to increase the temperature variation amount by emphasizing the temperature difference in the temperature difference image using the output function stored in the function storage unit 22, thereby producing a first emphasized image (a type of a temperature difference image) (Step S4). Further, the image processing unit 21 performs cumulative processing (a type of emphasizing processing) to enlarge the temperature variation amount by emphasizing the temperature difference in the first emphasized image, thereby producing a second emphasized image (a type of a temperature difference image) (Step S5). Further, using the information indicating the correlation stored in the defect storage unit 23, the image processing unit 21 determines a defect depth of the region where a local temperature variation occurs in the second emphasized image (Step S6). The image processing unit 21 then produces a defect determination image (a type of a temperature difference image) by converting the color of the region of the second emphasized image where the local temperature variation exists into a display color according to the determined defect depth (Step S7). The analysis unit 20 transmits image signals relating to the defect determination image to the image display unit 30 (Step S8). The image display unit 30 displays the defect determination image.

In the processing flow of FIG. 2, the image processing is performed in four stages ("Steps S2 and S3", "Step S4", "Step S5", and "Steps S6 and S7"). In this embodiment of the invention, the image processing in Steps S2 and S3 is indispensable, but the image processing of Steps S4 to S7 is optional. This means that the image processing in one or more of Steps S4 to S7 may be implemented, or none of Steps S4 to S7 may be implemented. It can be determined in advance whether or not the image processing of Steps S4 to S7 is to be implemented, or it can be determined, every time after completion of each image processing step, whether or not the subsequent processing step is to be implemented. Further, it can be determined either by the analysis unit 20 or by the operator whether or not the image processing in Steps S4 to S7 is to be implemented. If it is determined by the analysis unit 20, the analysis unit 20 may be designed to determine whether or not any region where a local temperature variation occurs can be distinguished from a temperature difference image produced in the directly preceding step. If it is determined by the operator, the temperature difference image produced in Steps S3, S4, and S5 is displayed on the image display unit 30 so that the operator can check the displayed temperature difference image to determine whether or not the subsequent image processing steps should be implemented. The operator manipulates an operation unit (not shown) to give instruction to the analysis unit 20 to perform the respective image processing of Steps S4 to S7.

The processing of Steps S2 to S7 shown in FIG. 2 will be described specifically.

Production of Temperature Difference Image:

Image processing performed in Step S2 of FIG. 2 will be described.

FIG. 3 shows, in a modeled form, a group of pixels arranged in a plurality of rows and columns produced in moving average processing.

An IR thermal image is composed, for example, of a group of pixels arranged in a plurality of rows and columns as shown in FIG. 3. Although FIG. 3 shows a group of pixels composed of 101×101 matrix, the numbers of rows and columns in the group are not limited to this. The image processing unit 21 uses this group of pixels to perform moving average processing as described below.

Firstly, an average temperature is computed with respect to a predetermined number of pixels, herein, with respect to a first pixel group consisting of pixels in the columns numbered 1 to 9 and in the rows numbered 1 to 9. The computed average temperature is substituted into the center pixel of the first pixel group (in the column numbered 5 and the row numbered 5). Subsequently, an average temperature is computed with respect to a second pixel group, which is shifted by one column from the first pixel group, consisting of pixels in the columns numbered 2 to 10 and in the rows numbered 1 to 9. The computed average temperature is substituted into the center pixel of the second pixel group (in the column numbered 6 and the row numbered 5). In this manner, sequentially shifting the pixel group by one column each time, an average temperature is computed with respect to the n-th pixel group consisting of pixels in the columns numbered n to (n+8) and in the rows numbered 1 to 9, and the computed average temperature is substituted into the center pixel of the n-th pixel group (in the column numbered ((n−1)+5) and the row numbered 5). Once there is no more column to shift the pixel group, the same processing as described above is carried out after shifting the pixel group by one row each time. Finally, an average temperature is computed with respect to the 8649-th pixel group consisting of pixels in the columns numbered 93 to 101 and in the rows numbered 93 to 101, and the computed average temperature is substituted into the center pixel of the 8649-th pixel group (in the column numbered 97 and the row numbered 97).

As described above, the processing is sequentially performed for obtaining an average of temperatures for each of pixel groups each consisting of a predetermined number of pixels (9×9 pixels in FIG. 3). This processing is called moving average processing. As a result of the moving average processing, an average temperature distribution image composed of pixels in the columns numbered 5 to 93 and the rows numbered 5 to 93 is obtained. In the moving average processing described above, the pixel group to be processed is shifted by one column each time until there is no more column to shift, and then the pixel group to be processed is returned to the initial column and shifted by one row each time. However, the processing according to the invention is not limited to this. What matters is that the average temperature distribution image composed of the pixels in the columns numbered 5 to 93 and the rows numbered 5 to 93 is obtained, and it doesn't matter in what sequence the processing is performed.

Next, the image processing performed in Step S3 of FIG. 2 will be described.

The image processing unit 21 computes a temperature difference at the same pixel (in the column numbered 5 to 93 and the row numbered 5 to 93) between the IR thermal image and the average temperature distribution image. A temperature difference image shown in FIG. 4 is produced based on the computation result. This temperature difference image is obtained by extracting distribution of a temperature variation other than the temperature gradient occurring on the structure surface from the IR thermal image. In other words, it can be said that the temperature difference image of FIG. 4 is obtained by removing the temperature gradient from the IR thermal image. If a defective region exists in the inside of the structure, a local temperature variation occurs in the part of the temperature difference image where the defective region is located. FIG. 4 shows a temperature difference image of a structure having a defect at a depth of 4 cm from the surface.

FIG. 5 is a graph representation showing temperature distribution in n columns of the IR thermal image and the temperature difference image. FIG. 6 shows the temperature distribution of FIG. 5 in a three-dimensional simulation image.

In FIG. 5 a defect exists between the pixel numbers a and b. The temperature distribution in the IR thermal image shows an upward curve in the graph as a whole due to the temperature gradient, which makes it difficult to distinguish between non-defective and defective regions. On the other hand, the temperature distribution in the temperature difference image indicates a temperature variation other than the temperature gradient. As seen from this, the temperature variation amount in the non-defective region is approximately zero whereas the temperature variation amount in the defective region is about 0.055 (=|0.035−(−0.02)|), and only the temperature variation in the defective region is emphasized. Accordingly, it is easy to distinguish between non-defective and defective regions. The "temperature variation amount" as used in the description with reference to FIG. 5 is represented by a difference between the maximum value and the minimum value (=|maximum−minimum|) of the temperature differences in the part where a local temperature variation has occurred.

Production of First Emphasized Image:

The emphasizing processing performed in Step S4 of FIG. 2 will be described. There is no problem if a local temperature variation can be discriminated based on the temperature difference image produced in Step S3. For example, there is no problem if the local temperature variation can be clearly discriminated based on the temperature difference image as shown in FIG. 4. In practice, however, a measurement error may be caused by the IR camera, or a temperature variation other than the temperature gradient may exist in the structure. In such cases, it becomes difficult to distinguish the local temperature variation even if using the temperature difference image. If the temperature of the structure surface is actually measured, there will be observed a temperature variation of ±0.025° C.

It is assumed that there is a variation in the temperature of the structure surface. When a temperature variation of ±0.025° C. is added to the temperature difference image shown in FIG. 4, for example, a temperature difference image as shown in FIG. 7 is obtained. Unlike the temperature difference image shown in FIG. 4, it is difficult to discern a local temperature variation in the temperature difference image shown in FIG. 7. If a temperature difference image as shown in FIG. 7 is obtained, emphasizing processing is performed to emphasize the temperature differences in the temperature difference image by using an output function as shown in FIG. 8.

FIG. 8 shows an example of output function stored in the function storage unit.

In the output function shown in FIG. 8, the output ratio (=output/input) becomes greater as the input value becomes greater. In this output function, the degree of emphasis of the output becomes greater as the input value becomes greater.

The image computation unit 21 reads the output function from the function storage unit 22, and inputs to the output function the temperature difference at each pixel of the temperature difference image to compute the output. A first emphasized image shown in FIG. 9 is produced based on the result of the computation. The first emphasized image is a type of a temperature difference image in which the temperature difference in the temperature difference image is emphasized. In the first emphasized image, the temperature variation is also enlarged, and thus the local temperature variation, that is, the defective region which is difficult to discriminate in the unemphasized temperature difference image is emphasized.

Production of Second Emphasized Image:

The emphasizing processing performed in Step S5 of FIG. 2 will be described.

There is no problem if a local temperature variation can be discriminated based on the first emphasized image produced in Step S4. However, it is sometimes difficult to discern a local temperature variation in the first emphasized image. In such a case, emphasizing processing is performed to emphasize the temperature differences in the first emphasized image. It should be noted that the emphasizing processing to be described below is similar in computing technique to the moving average processing implemented in Step S2. Herein, this emphasizing processing is referred to as cumulative processing.

FIG. 10 shows, in a modeled form, a group of pixels arranged in a plurality of rows and columns produced in the cumulative processing.

The first emphasized image is composed, for example, of the group of pixels as a matrix shown in FIG. 10. The first emphasized image shown in FIG. 10 is a part of the temperature difference image produced in Step S3. Although FIG. 10 shows a group of pixels composed of 16×16 matrix (the columns numbered 3 to 18 and the rows numbered 3 to 18), the invention is not limited to these numerical values. Using this group of pixels, the image processing unit 21 performs cumulative processing as described below.

Firstly, a cumulative temperature is computed with respect to a predetermined number of pixels, herein with respect to the first pixel group consisting of the pixels in the columns numbered 3 to 5 and the rows numbered 3 to 5, and the computed cumulative temperature is substituted into the center pixel of the first pixel group (in the column numbered 4 and the row numbered 4). Subsequently, the pixel group is shifted by one column to define a second pixel group consisting of the pixels in the columns numbered 4 to 6 and the rows numbered 3 to 5, and a cumulative temperature is computed with respect to the second pixel group. The computed cumulative temperature is substituted into the center pixel of the second pixel group (in the column numbered 5 and the row numbered 4). In this manner, sequentially shifting the pixel group by one column each time, a cumulative temperature is computed with respect to the n-th pixel group consisting of pixels of the columns numbered n to (n+2) and the rows numbered 3 to 5, and the computed cumulative temperature is substituted into the center pixel of the n-th pixel group (in the column numbered ((n−1)+4) and the row numbered 4). Once there is no more column to shift the pixel group, then similar processing to the above processing is performed after shifting the pixel group by one row each time. Finally, a cumulative temperature is computed with respect to the 256-th pixel group consisting of the pixels of the columns numbered 16 to 18 and the rows numbered 16 to 18, and the computed cumulative temperature is substituted into the center pixel of the 256-th pixel group (in the column numbered 17 and the row numbered 17).

As described above, the cumulative processing is performed sequentially for each of pixel groups each consisting of a predetermined number of pixels (in FIG. 10, each pixel group consisting of 3×3 pixels) to obtain an accumulated temperature. Based on the result of the cumulative processing, a second emphasized image is produced, consisting of the pixels in the columns numbered 4 to 17 and the rows numbered 4 to 17. The second emphasized image is shown in FIG. 11. Although in the cumulative processing described above, the pixel group to be processed is shifted by one column each time, and once there is no more column to shift the pixel group, the pixel group is then returned to the initial column and shifted by one row each time, the invention is not limited to this sequence. What matters is that the second emphasized image consisting of the pixels of the columns numbered 4 to 17 and the rows numbered 4 to 17 is obtained, and it doesn't matter in what sequence the processing is performed.

Further, in this embodiment of the invention, Step S5 is implemented after Step S4 of FIG. 2. Specifically, the second emphasized image is produced by emphasizing the first emphasized image produced in Step S4. However, Step S5 may be implemented after Step S3 of FIG. 2, without Step S4. In other words, the second emphasized image may be produced by emphasizing the temperature difference image produced in Step S3.

The second emphasized image is a type of a temperature difference image in which the temperature difference in a temperature difference image is emphasized. In the second emphasized image, the temperature variation is also enlarged, and the local temperature variation, that is, the defective region which is difficult to discriminate in the unemphasized temperature difference image is emphasized.

Production of Defect Determination Image:

The determination processing in Step S6 of FIG. 2 will be described.

In a temperature difference image, there is a correlation between a defect depth and a temperature variation amount in a region where a local temperature variation occurs. Accordingly, if there is a region where a local temperature variation occurs in the temperature difference image, the defect depth of that region can be estimated from the temperature variation amount. The correlation between the temperature variation amount indicated by the temperature difference image and the defect depth can be preliminarily obtained by actual measurement. Information relating to the correlation thus obtained is stored in the defect storage unit 23. The defect storage unit 23 stores, for example, information associating the temperature variation amounts of T1 to T2 (T1>T2) with the defect depth D1 and associating the temperature variation amounts of T2 to T3 (T2>T3) with the defect depth D2 (D2>D1).

The image computation unit 21 reads information from the defect storage unit 23 and determines, based on the read information, a defect depth corresponding to the temperature variation amount at each pixel of the temperature difference image. It is determined that there is no defect with respect to a region where there exists no local temperature variation. On the other hand, with respect to a region where a local temperature variation exists, it is determined that the defect depth of that region is one corresponding to the temperature variation amount at the center of that region (for example at the central part C of FIG. 5), the temperature variation amount corresponding to the maximum temperature difference (the positive side temperature difference and the negative side temperature difference).

The image processing implemented in Step S7 of FIG. 2 will be described.

The image computation unit 21 changes the display state of the part of the temperature difference image where a local temperature variation occurs, that is, the display state of the defective region, according to the defect depth determined in Step S6. In the present embodiment of the invention, the display color of the defective region is changed according to the defect depth. For example, the display color is set to red if the defect depth is small, the display color is set to yellow if the defect depth is medium, and the display color is set to blue if the defect depth is large. A defect determination image is produced in this manner. It should be noted that marks with various shapes according to defect depths may be displayed over respective defective regions instead of changing the display color according to the defect depths. What is important is that the defect depth can be discriminated at a glance by the display state.

FIG. 12 shows an IR thermal image of the structure, FIG. 13 shows a temperature difference image produced using the IR thermal image of FIG. 12, and FIG. 14 shows a defect determination image produced using the temperature difference image of FIG. 13.

The IR thermal image of FIG. 12 represents little difference between the defective region and the non-defective region, whereas the defect determination image of FIG. 14 exhibits not only difference between the defective region and the non-defective region but also the differences in depth of the defective region. If the defect depth is small, there is a risk of surface exfoliation and the structure is unsafe. By viewing the defect determination image in which defect depths are represented by the display colors as described above, the operator can determine that the region represented in red color is a region with a high degree of risk, the region represented in yellow color is a region with a medium degree of risk, and the region represented in blue color is a region with a low degree of risk.

These are the description of the specific processing of Steps S2 to S7 of FIG. 2.

Advantage of Temperature Difference:

In Step S7 of FIG. 2, the defect depth is determined using a temperature variation amount in the temperature difference image as an index. The advantage of this temperature variation amount will be described.

As is described in Japanese Patent Application Laid-open No. 2005-140622 filed by the present inventors, it has been found that the defect depth has a correlation with the slope between two change points of temperature distribution in an IR thermal image and the temperature difference between these change points, that is, the temperature variation amount.

FIGS. 15(a) to 15(d) show relationships between a temperature difference between two change points and a slope between these change points with respect to respective defect depths. FIGS. 15(a) to 15(d) show results obtained by performing FEM thermal analysis while changing the size of defective region, the thermal environment, and the width of defect. There is a correlation between a depth of the defective region and (slope/temperature difference) obtained by linealizing the slope of each graph itself depicted in FIGS. 15(a) to 15(d).

FIG. 16 shows a relationship between a defect depth and (slope/temperature difference) in FIGS. 15(a) to 15(d).

FIG. 16 indicates that the discrimination between defect depths of 2 cm and 4 cm is possible. On the other hand, it also indicates that the discrimination between defect depths of 6 cm and 8 cm is not possible. This means that, in some cases, it is impossible to discriminate the defect depth by using the slope between two change points of temperature distribution in an IR thermal image and the temperature difference between the two points. Furthermore, since this method requires manual operation for detection of the defective region itself, the defective region cannot be detected in real time.

In contrast, the temperature difference image according to the present embodiment represents magnitudes of a temperature variation excluding the temperature gradient. Even though being a one-dimensional index, this value contains elements such as the slope and the temperature difference shown in FIGS. 15)(a) to 15(d).

FIG. 17 shows a relationship between a defect depth and a temperature variation amount.

It should be noted that, in FIG. 17, the temperature variation amount in a region where the local temperature variation occurs is represented by an "absolute value of central part". Absolute values are used for the reason that, as shown in FIG. 17 the values of the temperature difference are reversed between positive and negative between day and night.

Unlike FIG. 16, FIG. 17 indicates that the discrimination among defect depths of 2 cm, 4 cm, 6 cm and 8 cm is possible. Further, as shown in FIG. 2, this method can be completely automated and is capable of detecting the defective region in real time.

Industrial Applicability

This invention is applicable to defect investigation of concrete structures in general including not only bridges and viaducts but also concrete buildings.

LIST OF REFERENCE NUMERALS

Figure 1:
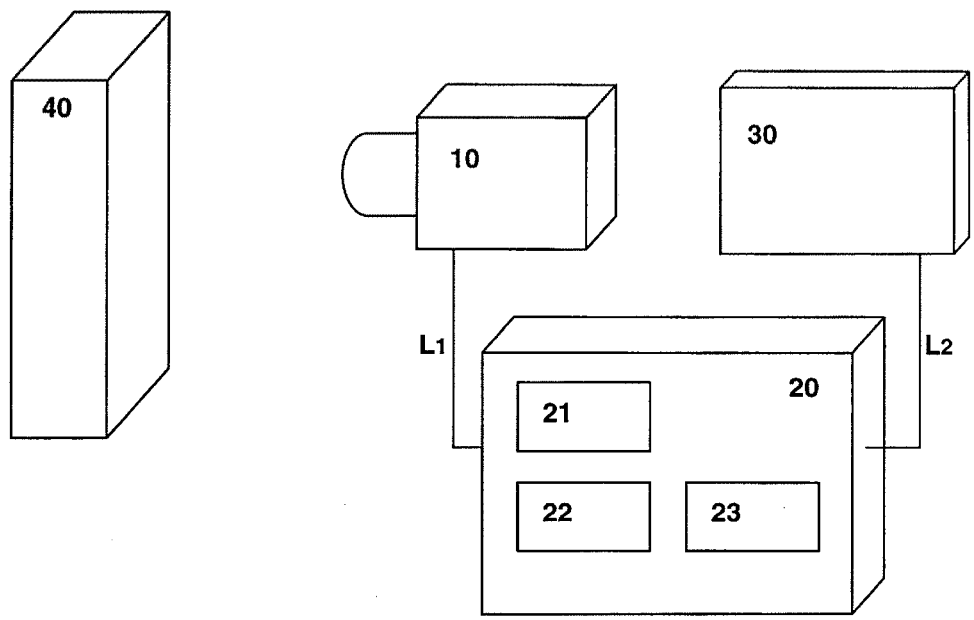
FIG. 1 is a functional block diagram showing a basic configuration of an IR thermal image analyzer according to an embodiment of the invention.
Figure 2:
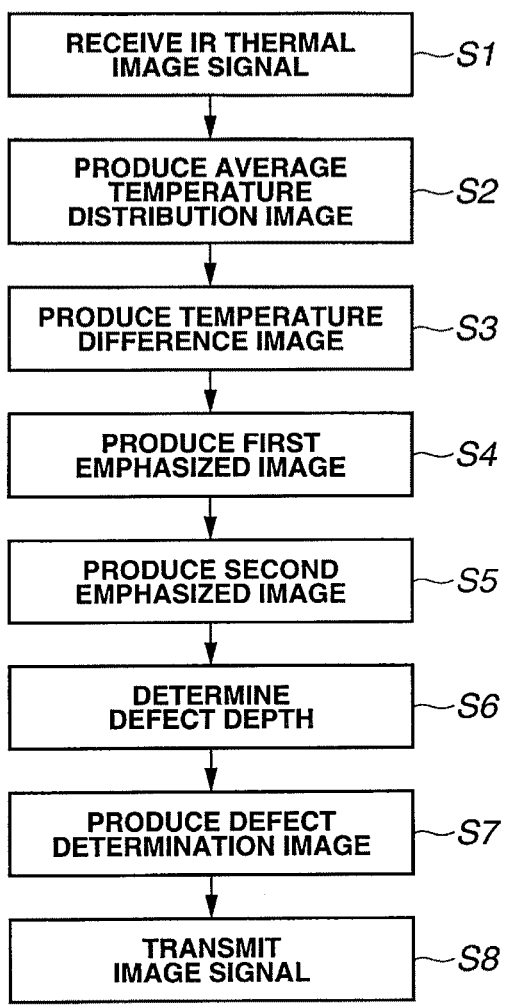
FIG. 2 is a diagram showing a flow of a series of processing performed by an analysis unit.
Figure 3:
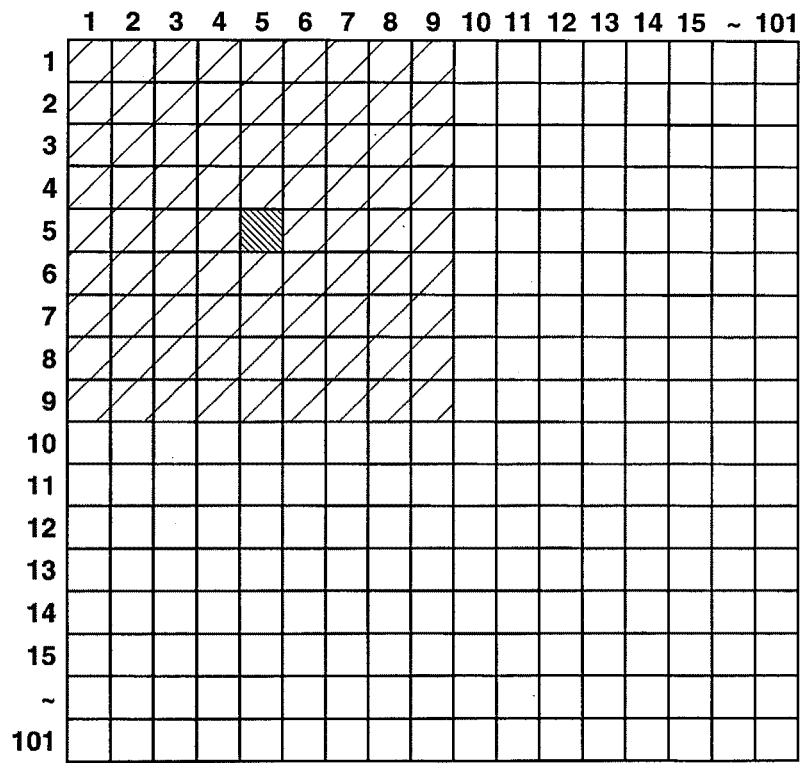
FIG. 3 is a diagram showing, in a modeled form, a group of pixels arranged in a plurality of rows and columns produced in moving average processing.
Figure 4:
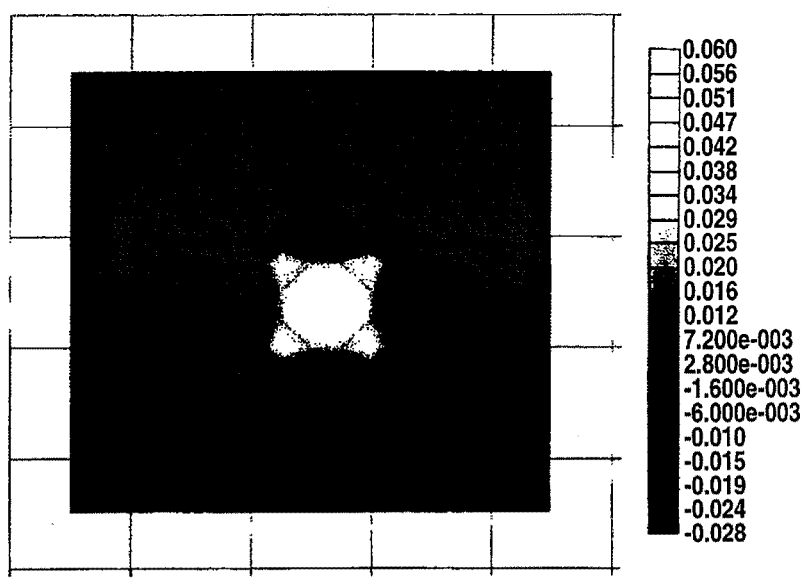
FIG. 4 is a diagram showing a temperature difference image.
Figure 5:
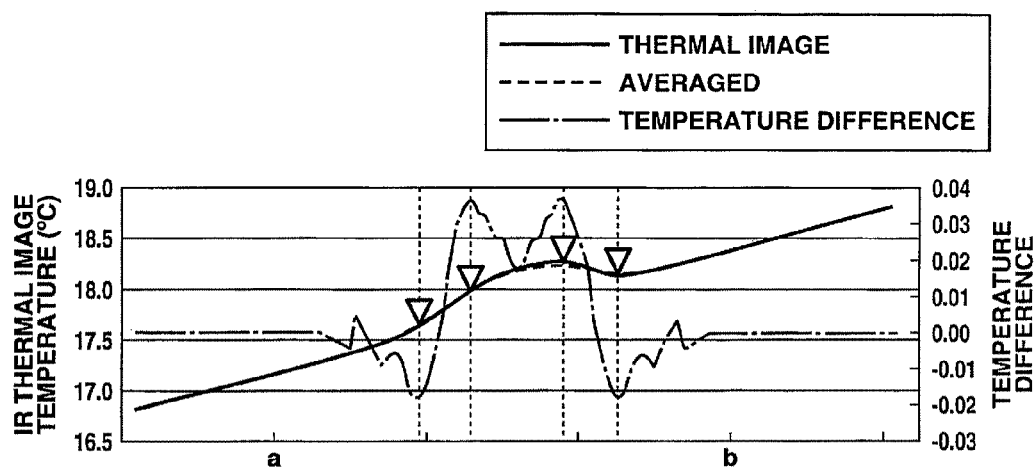
FIG. 5 is a graph representation of temperature distribution in n columns of an IR thermal image and a temperature difference image.
Figure 6:
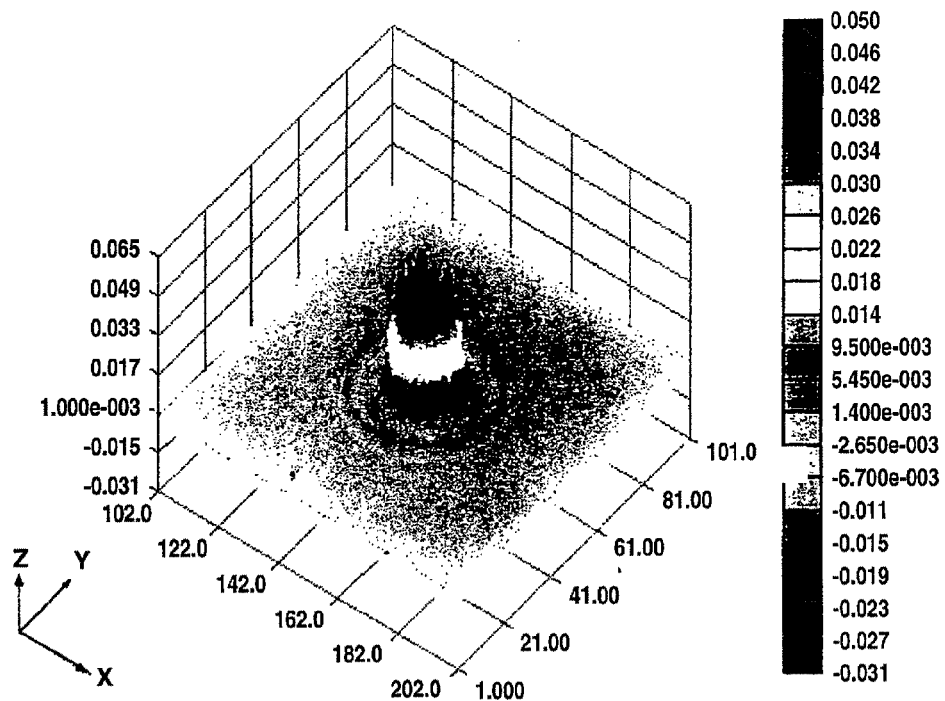
FIG. 6 is a diagram showing the temperature distribution of FIG. 5 in a three-dimensional simulation image.
Figure 7:
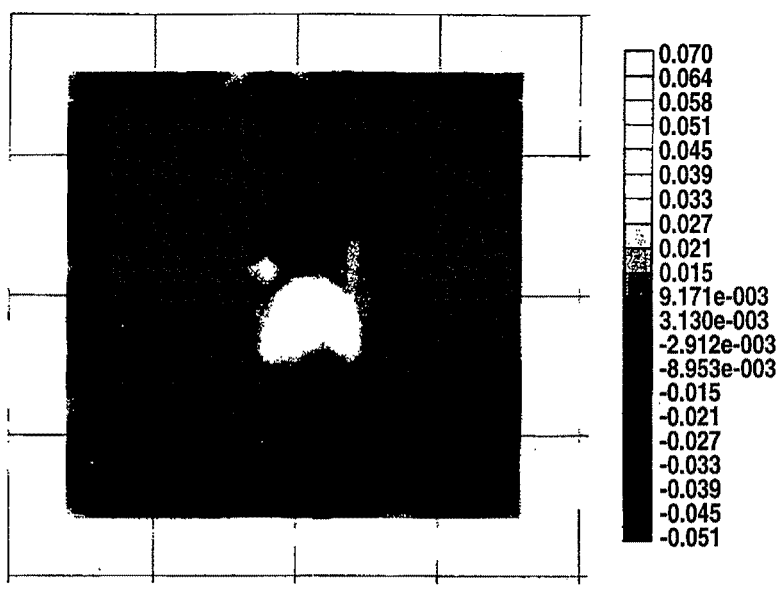
FIG. 7 is a diagram showing a temperature difference image in which a variation is added to the temperature difference image of FIG. 4.
Figure 8:
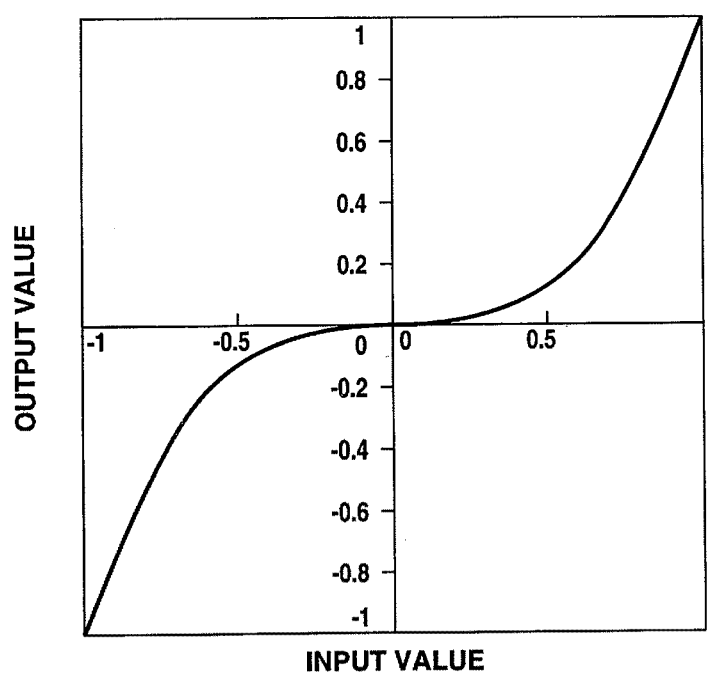
FIG. 8 is a diagram showing an example of an output function stored in a function storage unit.
Figure 9:
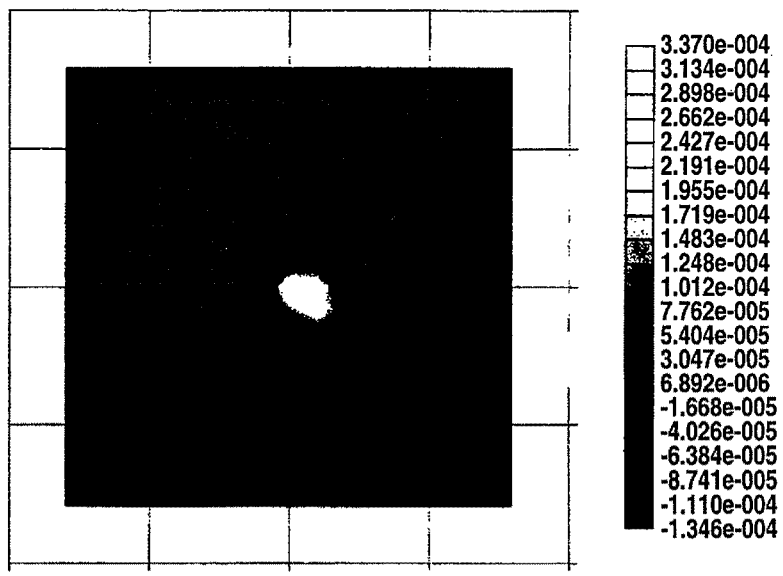
FIG. 9 is a diagram showing a first emphasized image.
Figure 10:
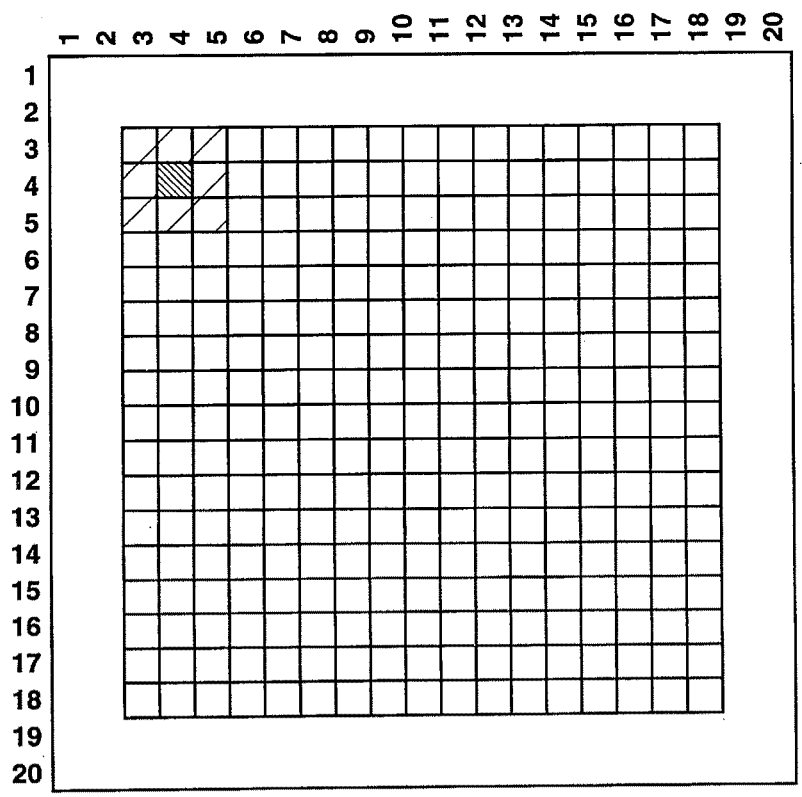
FIG. 10 is a diagram show, in a modeled form, a group of pixels arranged in a plurality of rows and columns produced in cumulative processing.
Figure 11:
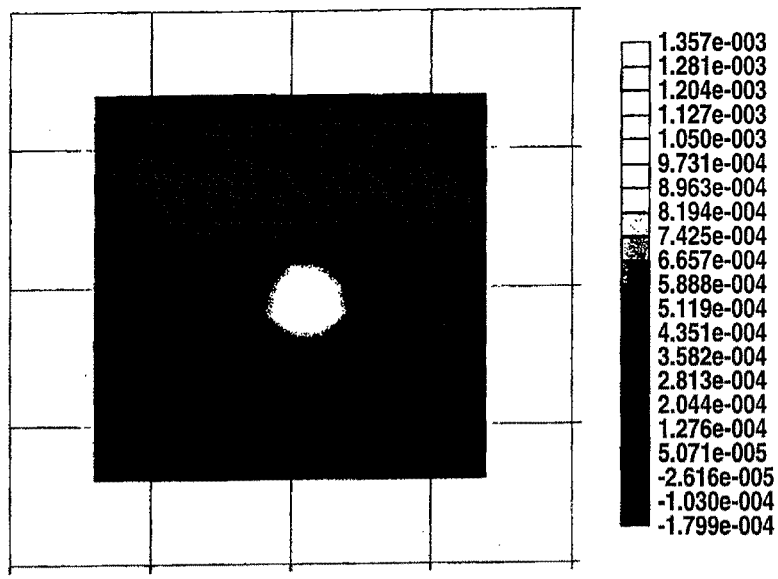
FIG. 11 is a diagram showing a second emphasized image.
Figure 12:
FIG. 12 is a diagram showing an IR thermal image of a structure.
Figure 13:
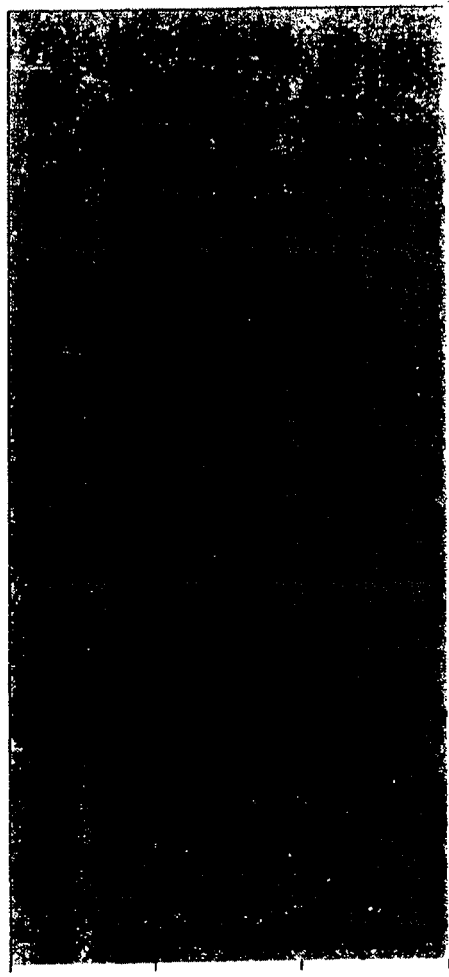
FIG. 13 is a diagram showing a temperature difference image produced using the IR thermal image of FIG. 12.
Figure 14:
FIG. 14 is a defect determination image produced using the temperature difference image of FIG. 13.
Figure 15A:
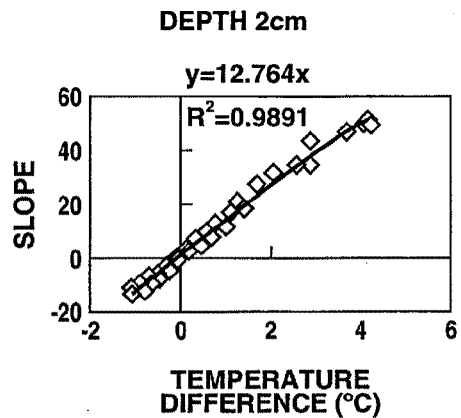
FIGS. 15(a) to 15(d) are diagrams showing relationship between a temperature difference between two change points and a slope between the change points for respective defect depths.
Figure 15C:
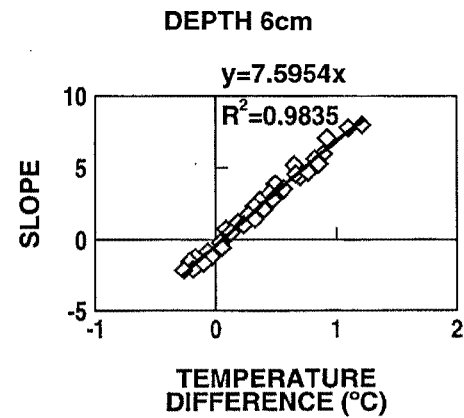
Figure 15B:
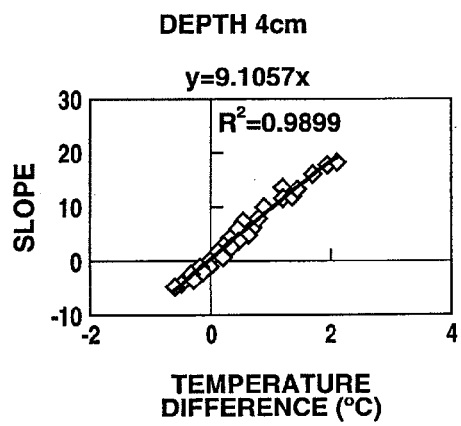
Figure 15D:
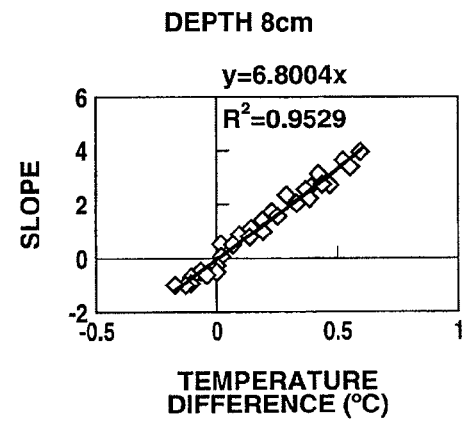
Figure 16:
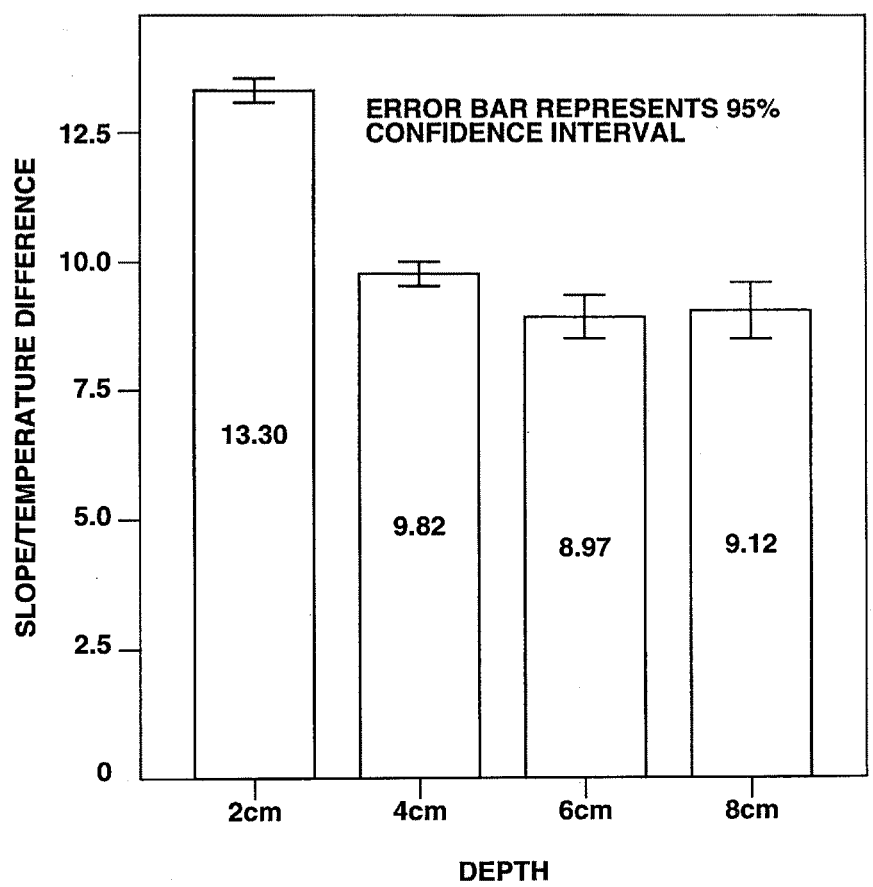
FIG. 16 is a diagram showing a relationship between a defect depth and (slope/temperature difference) of FIGS. 15(a) to 15(d)
Figure 17:
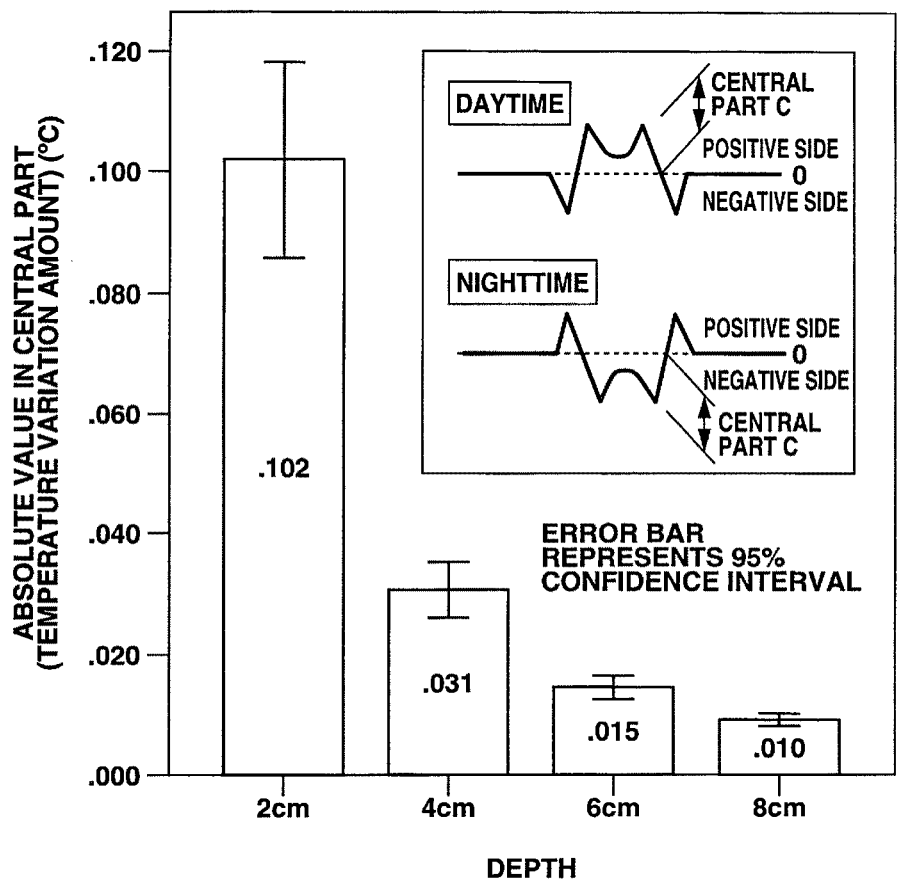
FIG. 17 is a diagram showing a relationship between a defect depth and a temperature variation amount.
Figure 18:
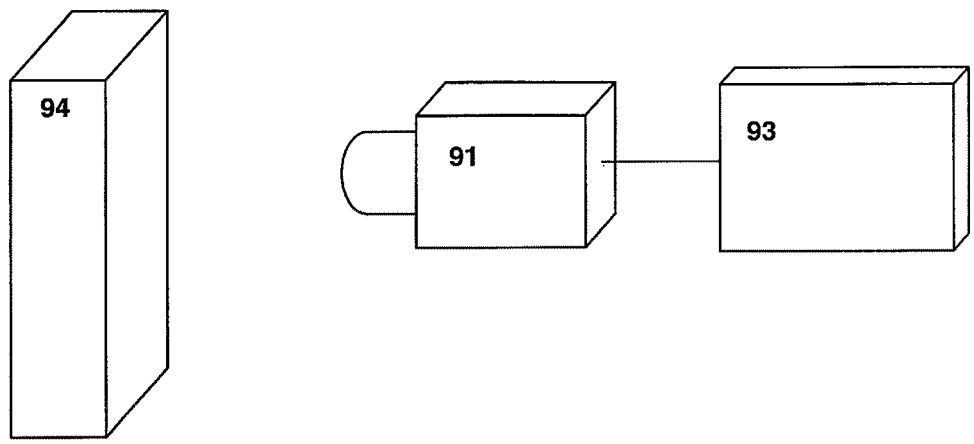
FIG. 18 is a diagram showing a basic configuration of a conventional IR thermal image analyzer.
Figure 19A:
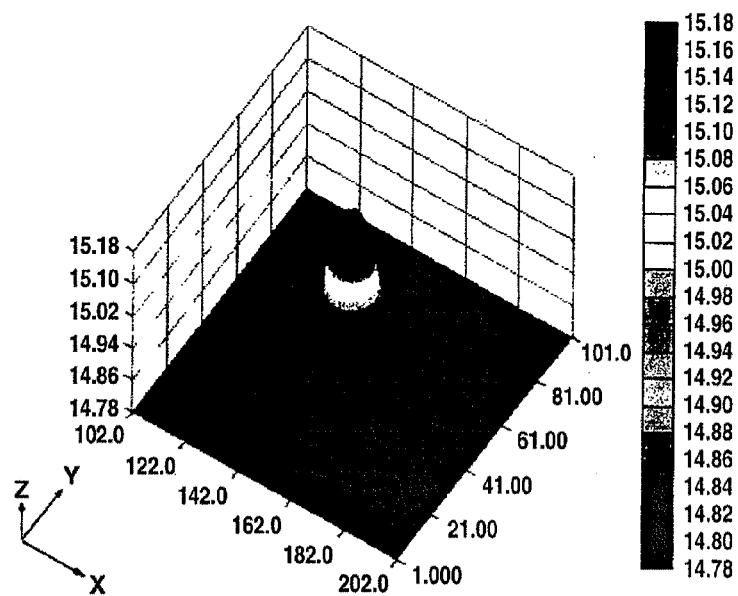
FIGS. 19(a) and 19(b) are a diagram showing temperature distribution on the structure surface.
Figure 19B:
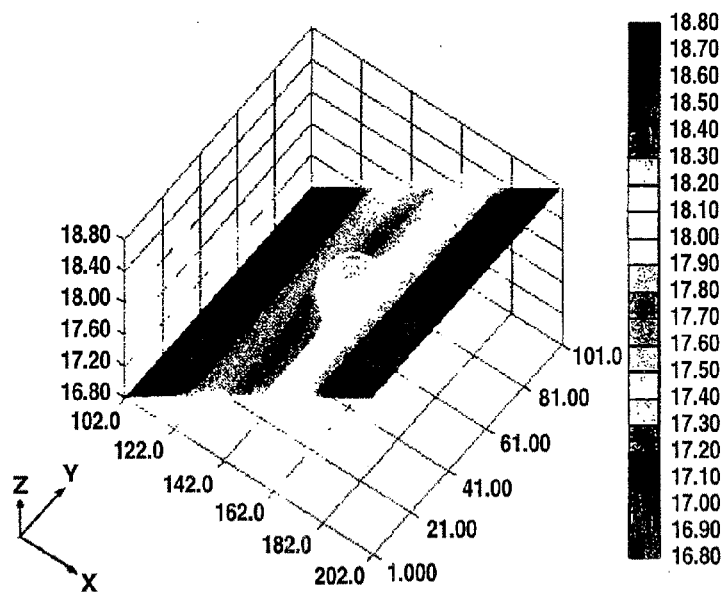

10: IR camera
20: Analysis unit
21: Image processing unit
22: Function storage unit
23: Defect storage unit
30: Image display unit
40: Structure

The invention claimed is:

1. An IR thermal image analyzer comprising:
an IR camera for taking an IR thermal image of a structure surface;
an image processing unit that produces an average temperature distribution image by performing moving average processing in which an average temperature is computed sequentially for each of pixel groups each consisting of a predetermined number of pixels in the IR thermal image, and produces an image indicating distribution of a temperature variation other than the temperature gradient by computing, temperature difference at a same pixel between the IR thermal image and the average temperature distribution image; and
an image display unit for displaying the image produced by the image processing unit.

2. The IR thermal image analyzer as claimed in claim 1, wherein the image processing unit performs emphasizing processing to emphasize the temperature difference in the temperature difference image, thereby producing an emphasized image in which the temperature difference in the temperature difference image is emphasized.

3. The IR thermal image analyzer as claimed in claim 1, further comprising a function storage unit for preliminarily storing an output function in which an output ratio becomes greater as an input value becomes greater,
wherein the image processing unit performs emphasizing processing for emphasizing the temperature difference at each pixel in the temperature difference image by inputting the temperature difference at each pixel in the temperature difference image into the output function and thus obtaining an output value, thereby producing an emphasized image in which the temperature difference in the temperature difference image is emphasized.

4. The IR thermal image analyzer as claimed in claim 1, wherein the image processing unit performs emphasizing processing for emphasizing the temperature difference in the temperature difference image by sequentially obtaining an accumulation of temperatures for each of pixel groups each consisting of a predetermined number of pixels in the temperature difference image, thereby producing an emphasized image in which the temperature difference in the temperature difference image is emphasized.

5. The IR thermal image analyzer as claimed in claim 1, further comprising a defect storage unit for preliminarily storing information indicating a correlation between a temperature variation amount in the temperature difference image and a defect depth of a defect located in the inside of the structure,
wherein the image processing unit obtains a defect depth in a part of the temperature difference image where a local temperature variation occurs by using the information, and produces a defect determination image in which a display state is changed in the part of the temperature difference image where the local temperature variation occurs according to the obtained defect depth.

6. The IR thermal image analyzer as claimed in claim 5, wherein the image processing unit obtains a defect depth corresponding to the temperature variation amount at a center of the part of the temperature difference image where local temperature variation occurs by using the correlation.

7. The IR thermal image analyzer as claimed in claim 1, wherein, in the moving average processing, an average temperature is computed with respect to a predetermined number of pixels and the computed average temperature is substituted into the center pixel of the pixels while shifting the pixels by one column or by one row, and an aggregate of the substituted center pixels forms the average temperature distribution image.

* * * * *